(12) United States Patent
Bonrath et al.

(10) Patent No.: US 10,029,970 B2
(45) Date of Patent: Jul. 24, 2018

(54) METHOD FOR PRODUCING SPECIFIC α, β-UNSATURATED ALDEHYDES

(71) Applicant: DSM IP ASSETS B.V., Heerlen (NL)

(72) Inventors: Werner Bonrath, Kaiseraugst (CH); Thomas Netscher, Kaiseraugst (CH); Jan Schuetz, Kaiseraugst (CH); Bettina Wuestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/518,355

(22) PCT Filed: Oct. 15, 2015

(86) PCT No.: PCT/EP2015/073873
§ 371 (c)(1),
(2) Date: Apr. 11, 2017

(87) PCT Pub. No.: WO2016/059152
PCT Pub. Date: Apr. 21, 2016

(65) Prior Publication Data
US 2017/0305827 A1 Oct. 26, 2017

(30) Foreign Application Priority Data
Oct. 16, 2014 (EP) ..................... 14189266

(51) Int. Cl.
| | | |
|---|---|---|
| *C07C 45/00* | (2006.01) |
| *C07C 403/00* | (2006.01) |
| *C07C 45/51* | (2006.01) |
| *C07C 47/225* | (2006.01) |
| *C07C 11/12* | (2006.01) |
| *C07C 5/23* | (2006.01) |

(52) U.S. Cl.
CPC ............. *C07C 45/512* (2013.01); *C07C 5/23* (2013.01); *C07C 11/12* (2013.01); *C07C 47/225* (2013.01); *C07C 2523/46* (2013.01); *C07C 2527/14* (2013.01); *C07C 2601/16* (2017.05)

(58) Field of Classification Search
CPC ........................... C07C 45/512; C07C 403/14
USPC ........................................................ 568/443
See application file for complete search history.

(56) References Cited

U.S. PATENT DOCUMENTS 3,994,936 A    11/1976   Andrews et al.

FOREIGN PATENT DOCUMENTS

| GB | 1 358 623 | 7/1974 |
| GB | 1 457 025 | 12/1976 |

OTHER PUBLICATIONS

International Search Report for PCT/EP2015/073873, dated Dec. 15, 2015, 4 pages.
Written Opinion of the ISA for PCT/EP2015/073873, dated Dec. 15, 2015, 6 pages.
Engel et al., "The Meyer-Schuster rearrangement for the synthesis of [alpha],[beta]-unsaturated carbonyl compounds", Organic & Biomolecular Chemistry, vol. 7, No. 20, Jan. 2009, p. 4149.
Cadierno et al., "Ruthenium-Catalyzed Isomerizations of Allylic and Propargylic Alcohols in Aqueous and Organic Media: Applications in Synthesis", Synlett, vol. 2008, No. 8, May 2008, pp. 1105-1124.

*Primary Examiner* — Sikarl A Witherspoon
(74) *Attorney, Agent, or Firm* — Nixon & Vanderhye P.C.

(57) ABSTRACT

The present invention relates to an improved method for producing specific α, β-unsaturated aldehydes.

10 Claims, No Drawings

METHOD FOR PRODUCING SPECIFIC α,β-UNSATURATED ALDEHYDES

This application is the U.S. national phase of International Application No. PCT/EP2015/073873 filed 15 Oct. 2015, which designated the U.S. and claims priority to EP Patent Application No. 14189266.1 filed 16 Oct. 2014, the entire contents of each of which are hereby incorporated by reference.

The present invention relates to an improved method for producing specific α,β-unsaturated aldehydes.

The specific α,β-unsaturated aldehydes which are aimed to be produced are represented by the following formula (I)

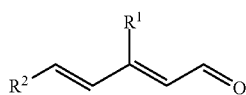

wherein
$R^1$ is a $C_1$-$C_4$-alkyl moiety, preferably —$CH_3$ or —$CH_2CH_3$, and
$R^2$ is

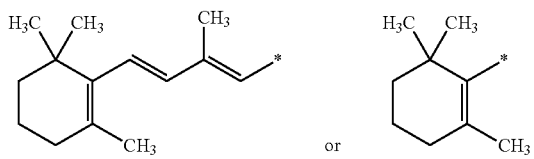

(the * is showing where the bond is localized).

These specific α,β-unsaturated aldehydes always have conjugated C—C-double bonds.

These specific α,β-unsaturated aldehydes are useful compounds. They can be used as such or they are useful intermediates to produce other compounds. For example compound (Ia)

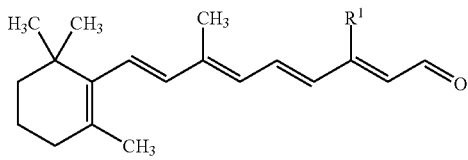

is used as an intermediate in the production of Vitamin A acetate (via a reduction followed by an acetylation).

Therefore due to the importance of such specific α,β-unsaturated aldehydes, there is always a need for improved methods of producing such compounds.

Now surprisingly, it was found that such specific α,β-unsaturated aldehydes having conjugated C—C-double bonds can be produced by a catalysed Meyer-Schuster rearrangement. The use of a Meyer-Schuster rearrangement to produce such compounds is not known.

The Meyer-Schuster rearrangement, which was published first in 1922 by Kurt Meyer and Kurt Schuster, is the chemical reaction described as an acid-catalyzed rearrangement of secondary and tertiary propargyl alcohols to α,β-unsaturated aldehydes.

The Meyer-Schuster rearrangement is usually carried out in acidic media using catalysts based on (transition) metals and/or metal oxides.

The goal of the present invention was to find an improved method for the production of compounds of formula (I).

Surprisingly it was found that a compound of formula (II)

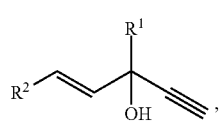

wherein $R^1$ and $R^2$ have the same meanings as defined in formula (I), can be used as starting material in a ruthenium-metal catalyzed Meyer-Schuster rearrangement to produce compounds of formula (I).

Therefore the present invention relates to a process (P) for the production of compounds of formula (I)

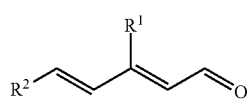

wherein
$R^1$ is a $C_1$-$C_4$-alkyl moiety, preferably —$CH_3$ or —$CH_2CH_3$, and
$R^2$ is

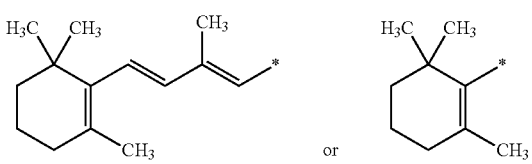

(the * is showing where the bond is localized)
by rearrangement of the compound of formula (II)

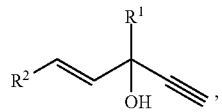

wherein $R^1$ and $R^2$ have the same meanings as in formula (I), characterized in that the process is carried out in the presence of at least one Ruthenium-metal catalyst.

It is not known from the prior art that such α,β-unsaturated aldehydes having conjugated C—C double bonds can be produced by this process The process according to the present invention is usually carried out as an "one-pot-reaction" under mild conditions resulting in good selectivity and yield. It can be carried out at very low temperature (room temperature!). Other catalysts like the commonly used Si-based catalysts need higher temperatures to react.

In a preferred embodiment of the present invention compounds of formula (IIa) or of formula (IIb)

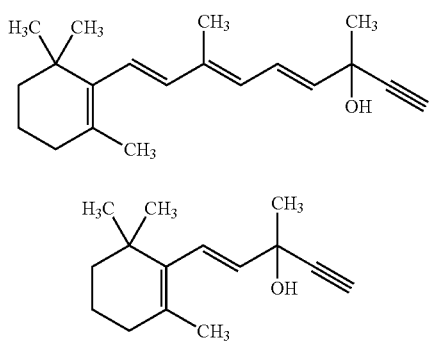
(IIa)

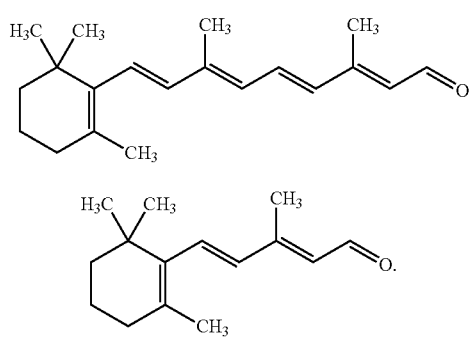
(IIb)

are used as starting material.

The corresponding products (when using compounds of formula (IIa) or of formula (IIb) as starting material) are those of formula (Ia) and of formula (Ib)

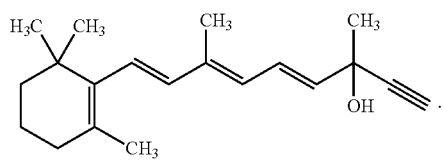
(Ia)

(Ib)

Therefore the present invention also relates to a process $(P_1)$, which is process (P), wherein the compound of formula (II) is the compound of formula (IIa)

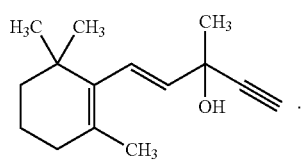
(IIa)

Therefore the present invention also relates to a process $(P_2)$, which is process (P), wherein the compound of formula (II) is the compound of formula (IIb)

(IIb)

A very preferred Ru-based catalyst is the following Ru-based catalyst of formula $(C^1)$

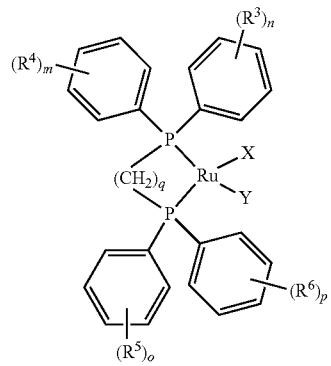
$C^1$ wherein $R^3$, $R^4$, $R^5$ and $R^6$ signify independently from each other —H, —$CH_3$, —$OCH_3$, —$NO_2$ or halogens and m, n, o and p signify independently from each other an integer 0, 1, 2 or 3, and X and Y signify independently from each other an allylic moiety, and q signifies an integer 1, 2, 3, 4, 5, or 6.

More preferred are catalysts according to formula $C^1$, wherein $R^3$, $R^4$, $R^5$ and $R^6$ signify the same substituent, and X and Y are the same allylic moiety, and q signifies an integer 2, 3, 4 or 5.

Especially preferred is the following Ru-based catalyst of formula $(C^{1\prime})$

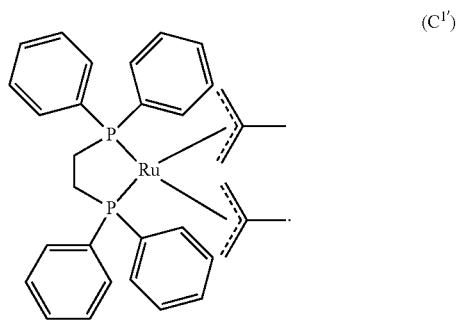
$(C^{1\prime})$

The catalysts of formula $(C^1)$ and of formula $(C^{1\prime})$ are known from the prior art and can be produced as described therein.

Therefore the present invention also relates to a process $(P_3)$, which is process (P), $(P_1)$ or $(P_2)$, wherein the transition metal based catalyst is a Ruthenium based catalyst.

Therefore the present invention also relates to a process $(P_3')$, which is process $(P_3)$, wherein the Ruthenium based catalyst is a catalyst of formula $(C^1)$

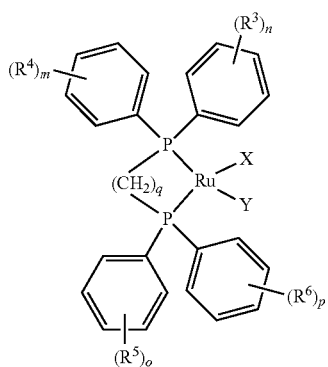

wherein
R³, R⁴, R⁵ and R⁶ signify independently from each other —H, —CH₃, —OCH₃ or —NO₂ Halogene?
m, n, o and p are independently from each other an integer 0, 1, 2 or 3,
X and Y are independently from each other an allylic moiety,
q signifies an integer 1, 2, 3, 4, 5, or 6.

Therefore the present invention also relates to a process (P₃"), which is process (P₃'), wherein R³, R⁴, R⁵ and R⁶ signify the same substituent, and
X and Y are the same allylic moiety, and
q signifies an integer 2, 3, 4 or 5.

Therefore the present invention also relates to a process (P₃'''), which is process (P₃), (P₃') or (P₃"), wherein the Ruthenium based catalyst is the catalyst of formula (01)

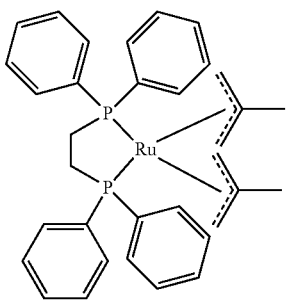

The substrate (starting material) to catalyst ratio (mol-based) is usually from 5000:1 to 10:1, preferably from 1000:1 to 20:1.

Therefore the present invention also relates to a process (P₄), which is process (P), (P₁), (P₂), (P₃), (P₃'), (P₃") or (P₃'''), wherein the substrate to catalyst ratio (mol-based) is from 5000:1 to 10:1, preferably from 1000:1 to 20:1.

The process according to the present invention is a Meyer-Schuster rearrangement. Mild reaction conditions are used for the process according to the present invention.

Usually the process according to the present invention is carried out in at least one non polar aprotic organic solvent and in the presence of at least one organic acid having a pK value in the range of about 4.0 to about 6.5.

All reactants are added together and mixed. The reaction mixture is heated to the temperature at which the transition metal-based catalytic rearrangement reaction occurs, to provide a resulting mixture.

As organic acids having a pK value in the range of about 4.0 to about 6.5 there come into consideration, inter alia, optionally halogenated, saturated and unsaturated aliphatic carboxylic acids, e.g. acetic acid (pK value 4.74), propionic acid (4.87), chloropropionic acid (3.98) and pivalic acid (5.01) or acrylic acid (4.25); alkanedicarboxylic acids, e.g. adipic acid (4.40); aryl-substituted alkanecarboxylic acids, e.g. phenylacetic acid (4.25); as well as aromatic carboxylic acids, e.g. benzoic acid (4.19) and 4-tert.butyl-benzoic acid (6.50).

The organic acids having a pK value in the range of about 4.0 to about 6.5 are added in at least equimolar amount in regard to the starting material (compound of formula (II)).

The reaction mixture is usually acidified after the first step has finished to react (usually after a few hours). The acidification step can be carried by using commonly known acids, such as for example sulphuric acid.

As solvents there can be used in the scope of the present invention in general non polar aprotic organic solvents, especially aliphatic, cyclic and aromatic hydrocarbons, such as, for example, $C_7$-$C_{10}$-alkanes, $C_5$-$C_7$-cycloalkanes, benzene, toluene and naphthalene as well as mixtures of such solvents with one another, e.g. paraffin oil (a mixture of saturated aliphatic hydrocarbons). As well as carboxylate esters, such as ethyl acetate.

The rearrangement according to the present invention usually comprises two steps:
(1) the rearrangement process is started with the addition of the starting material, the catalyst, the solvent as well as the organic acid having a pK value in the range of about 4.0 to about 6.5 (the sequence of adding these compounds is not of importance. Furthermore it is clear that it is also possible adding mixtures of each of the components as well.)
(2) and optionally afterwards the reaction mixture is acidified with an acid or a mixture of acids (such as i.e. sulfuric acid).

Therefore the present invention relates to a process (P₅), which is process (P), (P₁), (P₂), (P₃), (P₃'), (P₃"), (P₃''') or (P₄), characterized in that the rearrangement is carried out in at least one non polar or polar aprotic organic solvent in the presence of at least one organic acid having a pK value in the range of about 4.0 to about 6.5.

Therefore the present invention also relates to a process (P₅'), which is process (P₅), wherein the organic acid is chosen from the group consisting of acetic acid, propionic acid, chloropropionic acid, pivalic acid, acrylic acid, adipic acid, phenylacetic acid, benzoic acid and 4-tert.butyl-benzoic acid.

Therefore the present invention also relates to a process (P₅"), which is process (P₅) or (P₅'), wherein the organic acid is added in at least equimolar amount in regard to the starting material (compound of formula (II)).

Therefore the present invention also relates to a process (P₅'''), which is process (P₅), (P₅') or (P₅"), wherein the non polar or polar aprotic organic solvent is chosen from the group consisting of aliphatic, cyclic and aromatic hydrocarbons (such as $C_7$-$C_{10}$-alkanes, $C_5$-$C_7$-cycloalkanes, benzene, toluene, naphthalene, paraffin oil; as well as carboxylate esters, such as ethyl acetate.)

The process according to the present invention is usually carried out under very mild reaction conditions. The reaction temperature is usually between 10° C. and 50° C. Preferably between 20° and 40° C.

Therefore the present invention relates to a process (P₆), which is process (P), (P₁), (P₂), (P₃), (P₃'), (P₃"), (P₃'''), (P₄)

or (P₅), wherein the process is carried out at a reaction temperature of 10° C. to 50° C., preferably 20° C. to 40° C.

The products obtained by the process according to the present invention can be used as such or they can be used as intermediates for the production of other organic compounds. For example, the compound of formula (Ia) can be used in the production of Vitamin A acetate (via a reduction followed by an acetylation).

The same applies for the compound of formula (Ib), which can also be used in the production of Vitamin A acetate (compound (IIa) is the product of an aldol condensation of compound of formula (Ib) followed by an ethynylation).

The following Example illustrates the invention further without limiting it. All percentages and parts, which are given, are related to the weight and the temperatures are given in ° C., when not otherwise stated.

EXAMPLES

Example 1: 3-Methyl-5-(2,6,6-trimethylcyclohex-1-enyl)penta-2,4-dienal (Compound of Formula (Ib))

Ethynol (compound of formula IIb) (212 g, 0.90 mol) and benzoic acid (165.7 g, 1.35 mol, 1.5 eq.) were dissolved in 805 ml of ethyl acetate. The solution was set under argon atmosphere. In a counter flow of argon, 8.26 g (13.5 mmol, 1.5 mol %) of the ruthenium catalyst of formula (C¹') were added. Upon addition of the catalyst a slightly exothermic reaction was observed as the temperature of the reaction mixture increased from 24° C. to 31° C. After stirring for 23 hours at 24° C., TLC indicated that the reaction was complete. At the same temperature 8.8 ml of 10% sulfuric acid were added drop wise which caused a temperature increase to 35° C. After 23 hours at 24° C. the reaction was complete (TLC) and the dark brown reaction mixture was transferred into a 5-liter separation funnel, diluted with ethyl acetate (1 l) and washed with brine (2×1 l). The aqueous layers were re-extracted with ethyl acetate (1 l). The combined organic layers were dried over sodium sulfate, filtered and concentrated under reduced pressure (rotavap, 40° C. water-bath temperature). The crude product was dried for another 2 hours at 20 mbar resulting in a dark brown oil (233.5 g, ~75% purity, 88% yield). The product (compound of formula (Ib)) was then purified.

Example 2: Retinal (Compound of Formula (Ia))

C₂₀-propargyl alcohol (compound of formula IIa) (1.21 g, 4.0 mmol) and benzoic acid (0.736 g, 6.0 mmol, 1.5 eq.) were dissolved in 4.4 ml of ethyl acetate. The resulting yellow solution was set under argon atmosphere. In a counter flow of argon, 24.5 mg of ruthenium catalyst of formula (C¹') were added (slightly exothermic reaction, temperature increase to 30° C.). After stirring for 18 h at 24° C. TLC indicated that the acid addition was complete and 4 µl of diluted sulfuric acid (10%) were added (slightly exothermic reaction, temperature increase to 30° C.). After stirring for another 3 hours at 24° C., the reaction was complete (TLC). The dark brown reaction mixture was transferred into a 25-ml separation funnel, diluted with 5 ml of ethyl acetate, neutralized with aqueous NaHCO₃-solution (3×5 ml) (careful: gas evolution) and washed with water (2×5 ml) and brine (1×5 ml). The aqueous layers were re-extracted with 5 ml of ethyl acetate. The combined organic layers were dried over sodium sulfate, filtered and concentrated under reduced pressure (rotavap, 40° C. water-bath temperature). The crude product was obtained as dark brown oil in 67% yield (1.36 g, 56.3% purity) and purified.

The invention claimed is:
1. A process for producing a compound of formula (I):

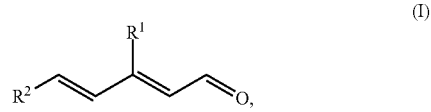

(I)

wherein
R¹ is a C₁-C₄-alkyl moiety, and
R² is

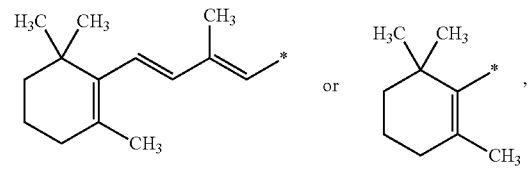

wherein
the process comprises conducting a rearrangement reaction of a compound of formula (II):

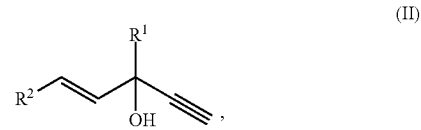

(II)

wherein
R¹ and R² in formula (II) have the same meanings as in formula (I), at a reaction temperature of 10° C. to 50° C. in the presence of at least one Ruthenium based catalyst to obtain the compound of formula (I).

2. The process according to claim 1, wherein the compound of formula (II) is a compound of formula (IIa)

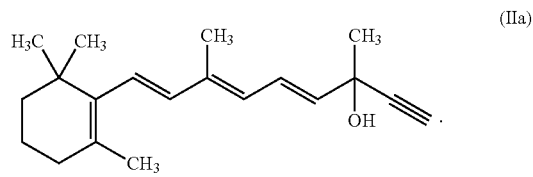 [SMILES: C#CC(C)(O)/C=C/C=C(C)/C=C/C1=C(C)CCCC1(C)C]

(IIa)

3. The process according to claim 1, wherein the compound of formula (II) is a compound of formula (IIb):

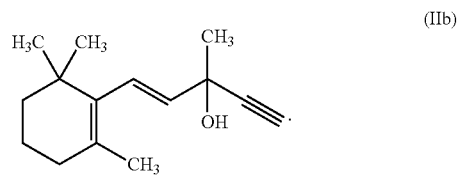 [SMILES: C#CC(C)(O)/C=C/C1=C(C)CCCC1(C)C]

(IIb)

4. The process according to claim 1, wherein the at least one Ruthenium catalyst is a catalyst of formula (C¹):

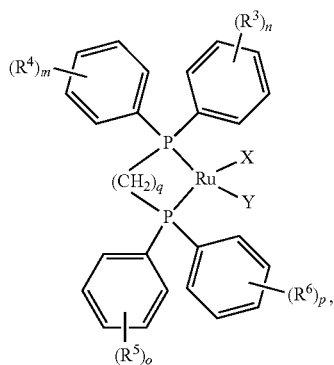

wherein

R³, R⁴, R⁵ and R⁶ signify independently from each other —H, —CH₃, —OCH₃, —NO₂ or halogene, m, n, o and p are independently from each other an integer of 0, 1, 2 or 3, X and Y are independently from each other an allylic moiety, and q signifies an integer of 1, 2, 3, 4, 5, or 6.

5. The process according to claim 1, wherein the at least one Ruthenium catalyst is a catalyst of formula (C¹'):

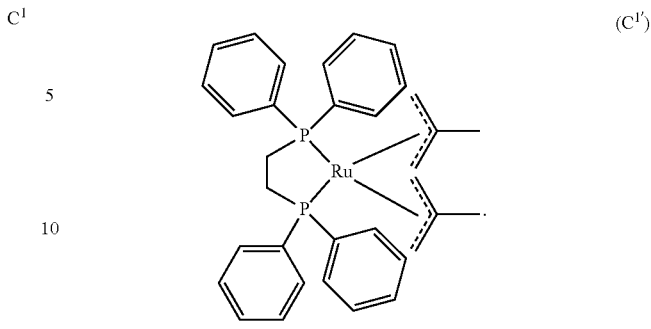

6. The process according to claim 1, wherein the at least one Ruthenium catalyst has a mol-based substrate to catalyst ratio which is from 5000:1 to 10:1.

7. The process according to claim 1, wherein the process is carried out in at least one non polar or polar aprotic organic solvent in the presence of at least one organic acid having a pK value in the range of 4.0 to about 6.5.

8. The process according to claim 1, wherein the process is carried out at a reaction temperature of 20° C. to 40° C.

9. The process according to claim 1, wherein R¹ in formulas (I) and (II) is —CH₃ or —CH₂CH₃.

10. The process according to claim 6, wherein the mol-based substrate to catalyst ratio of the at least one Ruthenium based catalysts is from 1000:1 to 20:1.

* * * * *